United States Patent [19]

Grau

[11] Patent Number: 4,959,351

[45] Date of Patent: Sep. 25, 1990

[54] CRYSTAL SUSPENSIONS OF INSULIN DERIVATIVES, PROCESSES FOR THEIR PREPARATION AND THEIR USE

[75] Inventor: Ulrich Grau, Hofheim am Taunus, Fed. Rep. of Germany

[73] Assignee: Hoescht Aktiengesellschaft, Frankfurt am Main, Fed. Rep. of Germany

[21] Appl. No.: 635,257

[22] Filed: Jul. 27, 1984

[30] Foreign Application Priority Data

Jul. 29, 1983 [DE] Fed. Rep. of Germany ....... 3327709

[51] Int. Cl.$^5$ ............................................. A61K 37/26
[52] U.S. Cl. ............................................. 514/4; 514/3; 530/303
[58] Field of Search ....................... 260/112.7; 514/3, 4

[56] References Cited

U.S. PATENT DOCUMENTS 2,920,014  1/1960  Petersen et al. .................. 260/112.7

FOREIGN PATENT DOCUMENTS 729670  5/1955  United Kingdom .

Primary Examiner—Frederick E. Waddell
Attorney, Agent, or Firm—Finnegan, Henderson, Farabow, Garrett and Dunner

[57] ABSTRACT

The invention relates to a process for the preparation of crystal suspensions of one or more insulin derivatives of the formula I

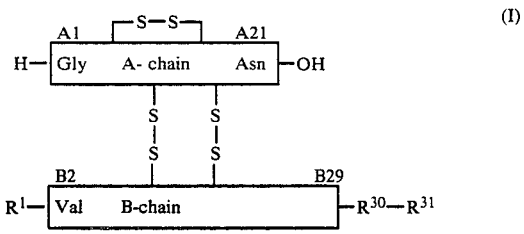

$R^1$ denotes H or H-Phe,
$R^{30}$ represents the radical of a neutral L-aminoacid which can be genetically coded and
$R^{31}$ represents a physiologically acceptable organic group of basic character with up to 50 carbon atoms, in the build-up of which 0 to 3 α-aminoacids participate and in which any terminal carboxyl function present can be free, as the ester function, as the amide function, as the lactone or reduced to $CH_2OH$, with an isoelectric point between 5.8 and 8.5, which comprises carrying out the crystallization in an aqueous medium close to the isoelectric point of the derivative or derivatives in the presence of an aromatic hydroxy compound, to crystals and crystal suspensions obtained by the process and to the use thereof.

20 Claims, 1 Drawing Sheet

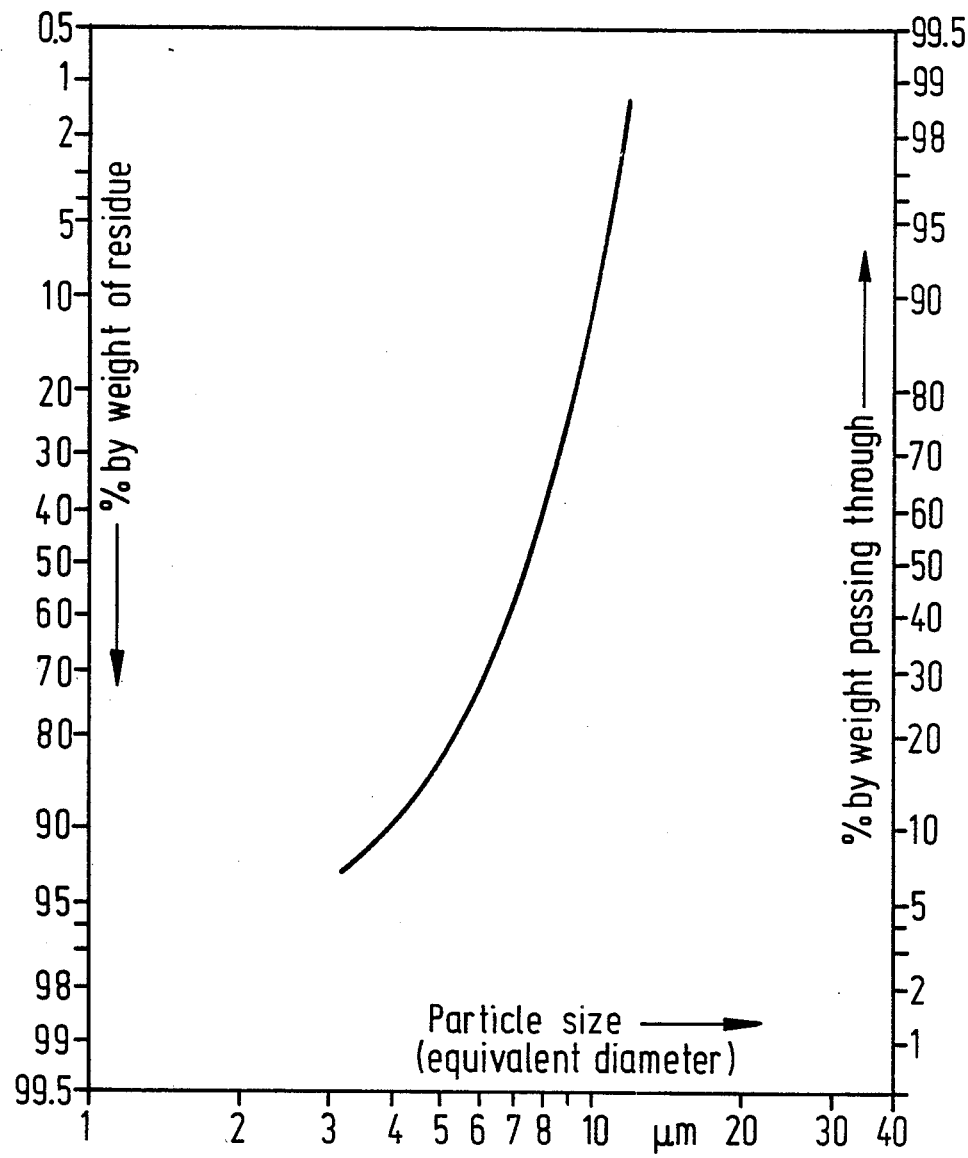

CRYSTAL SUSPENSIONS OF INSULIN DERIVATIVES, PROCESSES FOR THEIR PREPARATION AND THEIR USE

The crystallization of insulin is an intensively researched field, both in respect of work on structural analysis (Adams et al., Nature 224, 491 (1969), The Peking Insulin Structure Research Group, Sc. Sinica XVIII, 152–118 (1974)) and in respect of pharmaceutical applications (Schlichtkrull, Insulin-Kristalle (Insulin Crystals) (1961)). For therapeutic use as a delayed action form of insulin, a crystal size which can be defined as far as possible and usually should not exceed about 30 μm, so that there is a direct and reproducible relationship between the surface and the absolute amount of insulin, is of chief importance here. Defined redissolving kinetics are to be expected with such so-called monodisperse suspensions.

Examples of insulin crystal suspensions which are used therapeutically and have such properties are suspensions of rhombohedral zinc-insulin crystals which are about 25 μm in size, are stable in the presence of 0.8 to 2.5% of zinc (based on the weight of insulin) at a neutral pH value and exhibit a delayed action, and isophane insulin protamine crystals which are used in delayed action products in the form of small rods about 10 μm long and about 1 μm thick.

A few other crystal modifications of insulin are furthermore known, but these have hitherto been of interest only for X-ray structure analysis. Thus, zinc-free orthorhombic and monoclinic crystals have been obtained under acid pH conditions (Einstein, Low, Acta Cryst. 15, 32–34 (1962)). Smaller rhombic dodecahedra, which are to be classified in the cubic space group, have been obtained at the isoelectric point, also in the absence of zinc (Schlichtkrull, Insulin-Kristalle (Insulin Crystals) (1961)). Finally, a monoclinic crystal form of insulin has also been described, likewise by Schlichtkrull, which has been obtained above the isoelectric point in the presence of zinc and in the presence of phenol or phenol derivatives. These crystals grow to a considerable size (up to 3 mm) within a few days and have sharp edges. Interestingly, these crystals have been found only on glass surfaces and not on the free surface of the solution (Schlichtkrull, Insulin-Kristalle (Insulin Crystals), pages 57–60, (1961)).

Insulin derivatives which have at least one positive charge more in their net charge, so that their isoelectric point is shifted to higher pH values, are found to have different crystallization properties to insulin or proinsulin. These derivatives include, in particular, those derivatives which have an additional group of basic character on the C-terminus of the B chain, such as the proinsulin degradation products insulin—Arg$^{B31}$—OH and insulin—Arg$^{B31}$—Arg$^{32}$—OH, which are known to be found in pancreas extracts in small amounts. Other derivatives with similar properties are accessible by a semi-synthetic route. U.S. patent applications Ser. No. 632,845, filed July 20, 1984 (now abandoned in favor of application Ser. No. 873,476, filed July 20, 1984) and Ser. No. 632,856, filed June 6, 1986, relate to such insulin derivatives, processes for their preparation, agents containing them and their use.

They have, for example, other basic aminoacids or basic aminoacid derivatives (for example D-aminoacids, ornithine, hydroxylysine or argininol) instead of or in addition to arginine or an ester or amide grouping with simple alcohols or amines on the C-terminus. The alcohol or amide can be accompanied by an additional positive charge, such as, for example, in the insulin-(B30)-choline ester.

It has now been found, surprisingly, that these derivatives can be crystallized in the form of very uniformly shaped prisms about 10 μm in size from an aqueous medium in the presence of an aromatic hydroxy compound close to their isoelectric point.

The invention thus relates to a process for the preparation of crystal suspensions of one or more insulin derivatives of the formula I

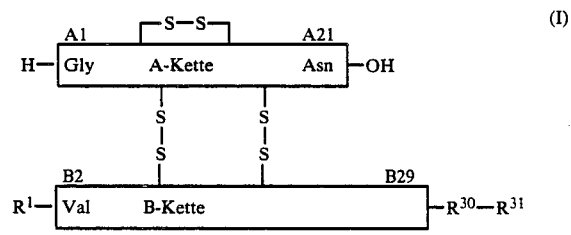

in which $R^1$ denotes H or H-Phe, $R^{30}$ represents the radical of a neutral L-aminoacid which can be genetically coded and $R^{31}$ represents a physiologically acceptable organic group of basic character with up to 50 carbon atoms, in the build-up of which 0 to 3 α-aminoacids participate and in which any terminal carboxyl function present can be free, as the ester function, as the amide function, as a lactone or reduced to $CH_2OH$, with an isoelectric point between 5.8 and 8.5, which comprises carrying out the crystallization in an aqueous medium close to the isoelectric point of the derivative or derivatives in the presence of an aromatic hydroxy compound.

Insulin derivatives of the formula I which are preferably crystallized are those in which $R^{31}$ represents a radical of the formula —$X_n$S, in which n=0, 1, 2 or 3, X represents identical or different radicals of naturally occurring neutral or basic L-aminoacids, preferably basic L-aminoacids, in particular Arg, Lys, His or Orn, and/or of the D-aminoacids corresponding to these, and S denotes OH or a physiologically acceptable group which blocks the carboxyl group and which, if n is 0, carries a positively charged or protonatable basic radical or, if n>0, can carry such a radical, and in which the C-terminus —X—S can also represent the radical of an aminoacid reduced to the corresponding alcohol or, if n=2 or 3, can represent the homoserine-lactone radical.

Insulin derivatives of the formula I in which $R^1$ represents H-Phe and/or $R^{30}$ represents Ala, Thr or Ser and/or X denotes the radical of a naturally occurring, basic L-aminoacid, such as Arg, Lys, Orn, Cit, Hyl or His, or the D-form thereof, are also particularly preferred.

Those peptides in which the radical $R^{31}$, if this contains aminoacid radicals or radicals of derivatives thereof (for example the corresponding alcohols or lactones), contains such radicals exclusively in the L-form, are furthermore particularly preferred.

The following L-aminoacids are genetically codable: Gly, Ala, Ser, Thr, Val, Leu, Ile, Asp, Asn, Glu, Gln, Cys, Met, Arg, Lys, His, Tyr, Phe, Trp and Pro (neutral aminoacids underlined).

A neutral, naturally occurring aminoacid is understood as meaning, in particular Gly, Ala, Ser, Thr, Val, Leu, Ile, Asn, Gln, Cys, Met, Tyr, Phe, Pro or Hyp. A basic, naturally occurring aminoacid is understood as meaning, in particular, Arg, Lys, Hyl, Orn, Cit or His.

Particularly suitable peptides of the formula I are those in which the C-terminus carries a group which blocks the carboxyl group from the series comprising ($C_1$ to $C_6$)-alkoxy, ($C_3$ to $C_6$)-cycloalkylalkoxy, $NH_2$, ($C_1$ to $C_6$)-alkylamino, di-($C_1$ to $C_6$)-alkylamino, amino-($C_1$ to $C_6$)-alkoxy, ($C_1$ to $C_4$)-alkylamino-($C_2$ to $C_6$)-alkoxy, di-($C_1$ to $C_4$)-ammonio-($C_2$ to $C_6$)-alkoxy, tri-($C_1$ to $C_4$)-ammonio-($C_2$ to $C_6$)-alkoxy, amino-($C_2$ to $C_6$)-alkylamino, [($C_1$ to $C_4$)-alkylamino]-($C_2$ to $C_6$)-alkylamino, [di-($C_1$ to $C_4$)-alkylamino]-($C_2$ to $C_6$)-alkylamino or tri-($C_1$ to $C_4$)-alkylammonio]-($C_2$ to $C_6$)-alkylamino.

Basic groups which block the carboxyl group are, in particular, $-O-[CH_2]_p-NR_2$, $-O-[CH_2]_p-NR_3$, $-NH-[CH_2]_p-NR_2$ or $-NH-[CH_2]_p-NR_3$, in which p is 2 to 6 and the radicals R are identical or different and represent hydrogen or ($C_1-C_4$)-alkyl.

The insulin derivatives of the formula I preferably have the sequence of human insulin, porcine insulin or bovine insulin.

For example, crystal suspensions of the following insulin derivatives can be obtained with the aid of the process according to the invention (without restricting the invention to these examples):

human insulin—$Arg^{31}$—OH
human insulin—$Arg^{31}$—$Ala^{B32}$—OH
porcine insulin—$Arg^{B31}$—OH
porcine insulin—$Arg^{B31}$—$Ala^{B32}$—OH
bovine insulin—$Arg^{B31}$—OH
bovine insulin—$Arg^{B31}$—$Arg^{B32}$—OH
des—$Phe^{B1}$—porcine insulin—$Arg^{B31}$—OH
des—$Phe^{B1}$—human insulin—$Arg^{B31}$—OH
des—$Phe^{B1}$—porcine insulin—$Arg^{B31}$—$Arg^{B32}$—OH
des—$Phe^{B1}$—human insulin—$Arg^{B31}$—$Arg^{B32}$—OH
porcine insulin—$Arg^{B31}$—$OCH_3$
human insulin—$Arg^{B31}$—$OCH_3$
bovine insulin—$Arg^{B31}$—$OCH_3$
porcine insulin—$Arg^{B31}$—$Arg^{B32}$—$OCH_3$
human insulin—$Arg^{B31}$—$Arg^{B32}$—$OCH_3$
Des—$Thr^{B30}$—human insulin—$Val^{B30}$—$Arg^{B31}$—OH
Des—$Thr^{B30}$—human insulin—$Val^{B30}$—$Ala^{B31}$—ArgB32—OH
human insulin—$Lys^{B31}$—OH
human insulin—D—$Arg^{B31}$—OH
human insulin—D—$Arg^{B31}$—$Arg^{B32}$—OH
human insulin—$Arg^{B31}$—D—$Arg^{B32}$—OH
human insulin—$Lys^{B31}$—$Arg^{B32}$—OH
human insulin—$Arg^{B31}$—$Lys^{B32}$—OH
human insulin—Argininol$^{B31}$
human insulin—$Val^{B31}$—$Arg^{B32}$—OH
human insulin—$Val^{B31}$—$Arg^{B32}$—$Arg^{B33}$—OH
human insulin—$Arg^{B31}$—Argininol$^{B32}$
human insulin—$Lys^{B31}$—$Arg^{B32}$—$Arg^{B33}$OH
human insulin human insulin-$Arg^{B31}$NH— 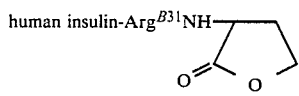

human insulin-$Arg^{B31}$—$Arg^{B32}$—NH— 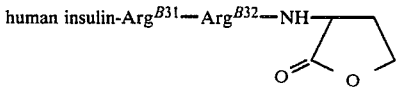

human insulin—$Arg^{B31}$—$NH_2$
human insulin—$Arg^{B31}$—$Arg^{B32}$—$NH_2$
human insulin—$Orn^{B31}$—OH
human insulin—$Leu^{B31}$—$Cit^{B32}$—OH
human insulin—(B30)—$OCH_2CH_2$—$NH_2$
human insulin—(B30)—NH—$CH_2CH_2$—$NH_2$
human insulin—$Arg^{B31}$O—$CH_2$—$CH_2$—$NH_2$
human insulin—$Arg^{B31}$—$CH_2$—$CH_2$—$N(CH_3)_2$
human insulin—(B30)—O—$CH_2$—$CH_2$—$N(CH_3)_3$
human insulin—(B30)—NH—$CH_2$—$CH_2$—$N(CH_3)_3$
human insulin—$Leu^{B31}$—O—$CH_2$—$CH_2$—$CH_2$—$N(C_2H_5)_3$
human insulin—$Trp^{B31}$—$Trp^{B32}$—TrpB33—$NH(CH_2)_6$—$N(n-Bu)_3$ The insulin derivatives of the formula I are prepared by (a) condensing a des-octapeptide (B23-30)-insulin of the formula II

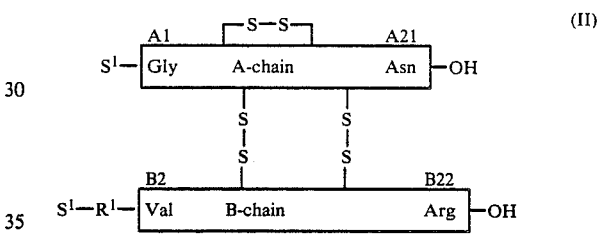

in which $R^1$ denotes Phe or a bond and $S^1$ denotes an amino-protective group which can be split off by proton solvolysis or by β-elimination, such as the tert.-butoxycarbonyl(Boc), the tert.-amyloxycarbonyl(Aoc) or the methylsulfonylethoxycarbonyl(Msc) radical, with a peptide of the formula III

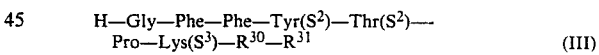

in which $R^{30}$ and $R^{31}$ have the meaning defined above, $S^2$ represents hydrogen, Bzl or $Bu^t$ and $S^3$ represent a urethane-protective group, such as Boc, Moc, Fmoc or Z, and, if necessary, any free COOH, OH, SH, ω-$NH_2$, guanidino and/or imidazole groups present in the radicals $R^{30}$ and $R^{31}$ are in protected form in a manner which is known per se, and, if appropriate, splitting off any protective groups present in a manner which is known per se, (b) reacting, in the presence of trypsin or a trypsin-like endopeptidase, a des-B30-insulin of the formula I, in which $R^1$ represents H or H-Phe and C-terminus $R^{30}$-$R^{31}$ together represents OH, with a compound of the formula V

in which $R^{30}$ and $R^{31}$ have the meanings defined above and in which, if necessary, the free COOH, OH, SH, ω-$NH_2$, guanidino and/or imidazole functions present are in protected form in a manner which is known per se, and, if appropriate, subsequently splitting off the protective groups present in a manner which is known per se, or (c) for the preparation of an insulin derivative with aminoacid radicals in $R^{31}$ in the L-configuration, chemically and/or enzymatically splitting a proinsulin, proinsulin derivative, preproinsulin or preproinsulin derivative or an intermediate of these compounds.

Des-Phe$^{B1}$-insulins as starting compounds are known, for example, from German Patent No. 2,005,658 or from European Patent A-No. 46,979.

The des-B30-insulins used as starting compounds in process variant b) are known, for example, from European Patent A-No. 46,979 or Hoppe-Seyler's Z. Physiol. Chem. 359/1978/799. The starting material of the formula IV used for variant (b) is prepared in a manner which is known per se by methods of peptide chemistry. Protective groups which can be used for IV are described in detail by M. Bodanzky et al., Peptide Synthesis, Ind. Ed. 1976, Wiley & Sons.

Human or primate proinsulin as the starting material for process variant (c) is meanwhile accessible by genetic engineering methods. The derivatives Arg(B31) and di-Arg(B31-32) are accessible therefrom by simple digestion with trypsin or trypsin-like enzymes. In addition, however, plasmids can also be constructed in a relatively simple manner and these lead to new insulin derivatives by splitting off corresponding preproinsulin derivatives, because they code other neutral or basic aminoacids instead of the arginines naturally occurring at B31 or B32.

The preparation of proinsulin using recombinant DNA methodology requires the formation of a DNA sequence for the aminoacid sequence of a proinsulin, which can be achieved either by isolation or by construction or by a combination of the two. The proinsulin-DNA is then inserted in the reading phase into a suitable cloning and expression carrier. The carrier serves to transform a suitable microorganism, and the transformed microorganism thereby obtained is then subjected to fermentation conditions, which lead to the formation of further copies of the proinsulin-containing vector and to the expression of proinsulin, a pure insulin derivative, a proinsulin precursor or a preproinsulin derivative.

If the expression product is a proinsulin precursor, such a product in general contains the proinsulin aminoacid sequence, which is bonded at its terminal amino group to a fragment of a protein, which is usually expressed by that of the gene sequence in which the proinsulin or proinsulin derivative has been inserted. The proinsulin aminoacid sequence is bonded to the protein fragment via a site which can be split specifically, which is, for example, methionine. The resulting proinsulin aminoacid sequence is split off from the fused gene product, for example as described in German Patent No. A-3,232,036, and the proinsulin is isolated, after purification.

The crystallization medium of the process according to the invention can contain zinc, the amount of zinc preferably being up to 1%, but in particular not more than 0.8%, based on the weight of insulin derivative. Only relatively small amounts of zinc of at most 40 µg/100 units, but preferably not more than 30 µg/100 units, are usually sufficient for the crystallization, and, in certain circumstances, these amounts can already be contained in the dry substance.

The crystallization is preferably carried out within a pH range of 1 pH unit below the isoelectric point to 1 pH unit above this point ($P_I \pm 1$). If appropriate, the pH can be adjusted with the aid of a buffer (for example phosphate, acetate or citrate).

The crystallization medium also contains phenol, cresol or a similar aromatic. The crystallization temperature is preferably 3° to 27° C., in particular 10° to 20° C. During the process, the suspension can be agitated slightly (for example stirred in a stirred vessel). The concentration of the insulin derivative of the formula I before the crystallization is preferably 0.2 to 40 mg/ml, in particular 1 to 7.5 mg/ml.

The crystals can also be obtained, for example, in a medium which already corresponds to the finished injection suspension (in the case of pure delayed action products). The (sterile) medium can accordingly already contain, besides phenol or similar aromatics and, where relevant, zinc, an isotonicity agent, such as, for example, NaCl or glycerol, and a buffer substance, such as, for example, sodium phosphate.

The invention furthermore relates to a crystal suspension of one or more insulin derivatives of the formula I which can be obtained by the abovementioned crystallization process, and to compounds of the formula I in the form of uniformly shaped crystals, which can be obtained by this crystallization process.

The crystal suspensions according to the invention can additionally contain (a) one or more insulin derivatives of the formula I in dissolved and/or amorphous form, (b) insulin and/or (c) proinsulin and/or (d) C-peptide in dissolved, amorphous and/or crystalline form. They can then also contain auxiliaries having a delaying action on the release of insulin, such as globin or protamine sulfate.

Besides the advantages in respect of crystal size and homogeneity thereof, the relatively low zinc content, which is below the concentration at which zinc is to be considered as a depot carrier, means that the crystal suspensions according to the invention are freely miscible with dissolved insulin. It is thus possible, for example, to combine insulin solutions with suspensions of the insulin derivative crystals before administration. The action profile of the medicament thus obtained can be controlled in an optimum manner by varying the content of the individual components.

If a higher zinc concentration were necessary for the stability of the crystals (as is the case, for example, with the zinc insulin rhombs), added, dissolved insulin would precipitate and would no longer act as a rapidly acting component.

Crystal suspensions of the derivatives described thus display, in an ideal manner, those properties which are desirable for the treatment of diabetes mellitus. The delayed action principle is inherent to the insulin derivative and is attributed to a phenomenon of protein chemistry, i.e. the sparing solubility at the isoelectric point.

The following examples serve to illustrate the invention further, without limiting the invention to these:

EXAMPLE 1

Porcine insulin—Arg$^{B31}$—Arg$^{B32}$—OH, prepared by tryptic digestion from porcine proinsulin, as a crystal suspension of prisms about 10 µm in size with 40 I.U./ml, and the size distribution thereof.

The following are mixed in water:

| Insulin-Arg$^{B31}$-Arg$^{B32}$-OH from pigs (27.0 I.U./mg) | 14.8 mg |
|---|---|
| sodium dihydrogen phospate dihydrate | 30.0 mg |
| m-cresol | 15.0 mg |
| phenol | 6.0 mg |
| glycerol | 16.0 mg |

The pH is brought to 7.4 with dilute NaOH and the total volume is brought to 10 ml with water. The batch is agitated slightly at 18° C. and prism-shaped crystals with sharp edges are formed, which grow very uniformly, are about 10 μm in size and exhibit extinction effects within a very small range of angles under polarized light. The size distribution of these crystals was measured with a Coulter Counter. The curve (see Figure) shows an extremely homogeneous size distribution; most of the crystals have an equivalent diameter (based on sperical particles) of 5 μm–10 μm.

EXAMPLE 2

Crystallization of a mixture of 50% of human insulin—Arg$^{B31}$—OH, prepared by tryptic splitting from prepro-insulin obtained by genetic engineering, and 50% of human insulin-B30-choline ester, prepared by semi-synthesis from porcine insulin, in a formulation with 40 I.U./ml, and the delayed action thereof.

The following are mixed in water:

| Human insulin-Arg$^{B31}$-OH (27.5 I.U./mg) | 7.3 mg |
|---|---|
| human insulin-(B30)-choline ester (28.0 I.U./mg) | 7.1 mg |
| sodium dihydrogen phosphate dihydrate | 21.0 mg |
| m-cresol | 15.0 |
| phenol | 0.6 mg |
| glycerol | 16.0 mg |

The pH is brought to 7.0 with dilute total volume is made up to 10 ml with water. The batch is agitated slightly at room temperature, whereupon prism-shaped crystals about 10 μm in size are formed. Such a suspension exhibits a greatly delayed action in rabbits at a dosage of 4.0 I.U./kg. The blood glucose values (in % of the starting values) are (n = 12 animals):

| t(hours) | 0 | 1 | 2 | 4 | 6 |
|---|---|---|---|---|---|
| blood glucose | 100% | 51% | 44% | 69% | 83% |

EXAMPLE 3

Suspension of crystalline human insulin—Arg$^{B31}$-Lys—$^{B32}$—OCH$_3$, prepared by semi-synthesis from porcine insulin, mixed with 50% of isophane protamine human insulin crystals with 100 I.U./ml.

The following are dissolved in a total volume of 10 ml in water:

| Human insulin-Arg$^{B31}$-Lys$^{B31}$-OCH$_3$ (27.0 I.U./mg), zinc-free | 37.0 mg |
|---|---|
| zinc chloride | 0.6 mg |
| sodium dihydrogen phosphate dihydrate | 21.0 mg |
| m-cresol | 15.0 mg |
| phenol | 6.0 mg |
| glycerol | 160.0 mg |

The pH is brought to 7.4 with 1 N HCl or 1 N NaOH. The batch is stirred slowly at room temperature, prism-shaped crystals being formed within one day. Isophane human insulin crystals (NPH) are prepared separately, by mixing the following in water:

| Human insulin (28.0 I.U./mg) | 35.7 mg |
|---|---|
| protamine sulfate | 3.2 mg |
| sodium dihydrogen phosphate dihydrate | 21.0 mg |
| m-cresol | 15.0 mg |
| phenol | 6.0 mg |
| glycerol | 160.0 mg |

The pH is brought to 7.4 with 1 N HCl or 1 N NaOH and the mixture is made up to 10 ml with water. The batch is stirred slowly, whereupon the typically rod-shaped NPH crystals are formed.

The two suspensions are brought together, whereupon the desired mixed product with 100 I.U./ml is formed, this product exhibiting a greatly delayed action in animal experiments.

EXAMPLE 4

Depot product with 40 I.U./ml containing 75% of crystalline human insulin—Arg$^{B31}$—Arg$^{B32}$—OH, obtained by tryptic splitting from preproinsulin obtained by genetic engineering, and 25% of human insulin in dissolved form.

The following are dissolved in 250 ml of dilute HCl: 1.111 g of human insulin—Arg$^{B31}$—Arg$^{B32}$—OH (27.0 I.U./mg), such that the pH is 4.0. This solution is sterilized by filtration in a suitable manner.

The following are dissolved separately in water:

| Sodium dihydrogen phosphate dihydrate | 1.575 g |
|---|---|
| m-cresol | 1.125 g |
| phenol | 0.450 g |
| glycerol | 14.118 g |

The pH is brought to 7.5 with 1 N NaOH and the mixture is made up to 0.5 liter with water. This buffer solution is likewise sterilized by filtration in a suitable manner.

Under aseptic conditions, the two sterile solutions are brought together, with stirring, and stirring is continued until homogeneous crystals about 10 μm in size have formed (A). An insulin solution (B) is prepared by mixing:

| Human insulin (28.0 I.U./mg) | 0.357 g |
|---|---|
| sodium dihydrogen phosphate dihydrate | 0.525 g |
| m-cresol | 0.375 g |
| phenol | 0.150 g |
| glycerol | 4.706 g |

The solution is brought to pH 7.3 with dilute NaOH and made up to 0.25 liter with water. This solution is sterilized by filtration. Under aseptic conditions, the insulin solution (B) is added to the crystal suspension (A), and suitable multi-withdrawal bottles are filled with the product.

Such a depot product can be used for the treatment of diabetes mellitus.

BRIEF DESCRIPTION OF DRAWING

The drawing figure shows the distribution of particle sizes (equivalent diameters measured using a Coulter counter) of crystals of porcine insulin—Arg$^{B31}$—Arg$^{B32}$—OH prepared by the method of Example 1.

I claim:

1. A process for the preparation of a suspension of crystals of substantially uniform particle size and substantially uniform shape suitable for injection of at least one insulin derivative of the formula I

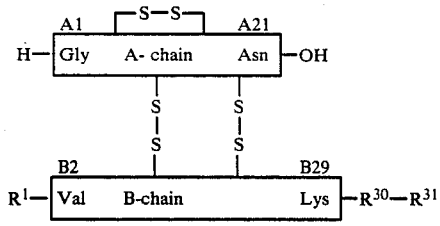

in which
R$^1$ denotes H or H-Phe,
R$^{30}$ represents the radical of Ala, Thr or Ser and
R$^{31}$ represents a physiologically acceptable organic group of basic character of the formula $X_n$-S which has up to 50 carbon atoms, in which n is 0, 1, 2 or 3
   X represents identical or different radicals of naturally occurring basic L-amino acids or of the corresponding D-amino acids or both and
   S denotes OH or a physiologically acceptable protective group which blocks the carboxyl group, but S being, if n is 0, a positively charged or protonatable basic radical and, if n is greater than 0, S can carry such a radical
and which contains or does not contain a terminal carboxyl function or an ester or an amide thereof, with an isoelectric point between 5.8 and 8.5, which comprises carrying out the crystallization in an aqueous medium closes to the isoelectric point of the derivative in the presence of at least one phenol and of glycerol as an isotonicity agent.

2. The process as claimed in claim 1, wherein R$^1$ in the formula I represents H-Phe.

3. The process as claimed in claim 1, wherein the crystallization is carried out at a temperature of 3°–27° C.

4. The process as claimed in claim 1, wherein the concentration of the insulin derivative (I) in the crystallization medium is 0.2 to 40 mg/ml.

5. A crystal suspension suitable for injection of at least one insulin derivative of the formula I, obtainable by a process as claimed in claim 1.

6. A crystal suspension as claimed in claim 5, which additionally contains an auxiliary with a delaying action.

7. A process as claimed in claim 1, wherein, if R$^{31}$ contains the ester group of a carboxyl function and if n is 2 or 3, $X_n$-S represents the homoserine-lactone radical.

8. A process as claimed in claim 1, wherein X in formula I represents the radical of Arg, Lys or both.

9. A process as claimed in claim 1, wherein the crystallization is carried out in the presence of up to 1%, based on the weight of insulin, of zinc.

10. A process as claimed in claim 1, wherein the crystallization medium is buffered by a buffer substance.

11. A process as claimed in claim 3, wherein the crystallization is carried out at a temperature in the range from 10° to 20° C.

12. A process as claimed in claim 1, wherein the crystallization is carried out within a pH-range of 1 pH unit below the isoelectric point to 1 pH unit above this point.

13. A process as claimed in claim 1, wherein the crystallization is carried out in the presence of phenol, cresol or a mixture thereof.

14. A process as claimed in claim 10, wherein the buffer substance is a phosphate or citrate.

15. A process as claimed in claim 1 for the preparation of a suspension of crystals of substantially uniform particle size and substantially uniform shape of at least one insulin derivative of the formula I

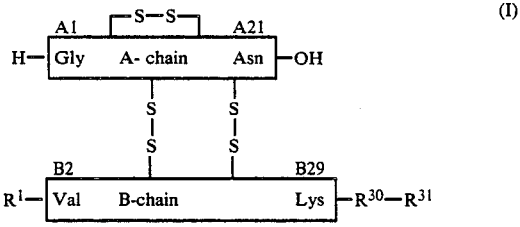

in which
R$^1$ denotes H or H-Phe,
R$^{30}$ represents the radical of Ala, Thr or Ser and
R31 represents a physiologically acceptable organic group of basic character of the formula $X_n$-S which has up to 50 carbon atoms, in which
n is 0, 1, 2 or 3
   X represents identical or different radicals of naturally occurring basic L-amino acids or of the corresponding D-amino acid or both and
   S denotes OH or a physiologically acceptable protective group which blocks the carboxyl group, but S being, if n is 0, a positively charged or protonatable basic radical and, if n is greater than 0, S can carry such a radical
and which contains or does not contain a terminal carboxyl function or an ester or an amide thereof, with an isoelectric point between 5.8 and 8.5, which comprises carrying out the crystallization in an aqueous medium within a pH range of 1 pH unit below the isoelectric point to 1 pH unit above this point in the presence of phenol, cresol or a mixture thereof and of glycerol as an isotonicity agent at a temperature in the range of 3° to 27° C., the concentration of the insulin derivative (I) in the crystallization medium being in the range from 0.2 to 40 mg/ml.

16. A crystal suspension as claimed in claim 5, which additionally contains at least one compound selected from the group consisting of (a) an insulin derivative of the formula I in a non-crystallized form, (b) insulin, (c) proinsulin and (d) C-peptide.

17. A compound of the formula I as defined in claim 1 in the form of uniformly shaped crystals.

18. A compound of the formula I as defined in claim 1 in the form of uniformly shaped prisms.

19. A compound as claimed in claim 18, wherein the prisms are about 10 μm in size.

20. A process according to claim 1, wherein the phenol is present in an amount of at least 1.56 g/l and the glycerol is present in an amount of at least 1.6 g/l of the aqueous crystallization medium.

* * * * *